United States Patent
Purcell

(10) Patent No.: US 8,075,594 B2
(45) Date of Patent: Dec. 13, 2011

(54) MULTI-AXIAL TRANSVERSE ROD CONNECTOR

(75) Inventor: Thomas Purcell, Del Mar, CA (US)

(73) Assignee: Alphatec Spine, Inc, Carlsbad, CA (US)

( * ) Notice: Subject to any disclaimer, the term of this patent is extended or adjusted under 35 U.S.C. 154(b) by 775 days.

(21) Appl. No.: 11/973,709

(22) Filed: Oct. 9, 2007

(65) Prior Publication Data

US 2008/0103507 A1    May 1, 2008

Related U.S. Application Data

(60) Provisional application No. 60/849,871, filed on Oct. 6, 2006.

(51) Int. Cl.
*A61B 17/70* (2006.01)
(52) U.S. Cl. .................................................. 606/252
(58) Field of Classification Search ........... 606/246–279
See application file for complete search history.

(56) References Cited

U.S. PATENT DOCUMENTS

| | | | |
|---|---|---|---|
| 2002/0143330 A1* | 10/2002 | Shluzas | ........................... 606/61 |
| 2002/0169448 A1 | 11/2002 | Vanacker | |
| 2004/0049188 A1 | 3/2004 | Slivka et al. | |
| 2004/0133203 A1* | 7/2004 | Young et al. | ..................... 606/61 |
| 2005/0107789 A1* | 5/2005 | Sweeney | ........................ 606/61 |
| 2005/0228377 A1 | 10/2005 | Chao et al. | |

FOREIGN PATENT DOCUMENTS

EP    1 302 169 A1    4/2003

OTHER PUBLICATIONS

International Search Report for Application No. PCT/US2007/021655 dated May 8, 2008.

* cited by examiner

*Primary Examiner* — Eduardo C Robert
*Assistant Examiner* — Summer Kostelnik
(74) *Attorney, Agent, or Firm* — Michael R. Shevlin

(57) ABSTRACT

A multi-axial rod connector for connecting spinal rods is provided. The rod connector includes a poly-axial rod assembly configured to include a lateral translation mechanism and a fixed hook configured to be rigidly coupled to one end of the poly-axial rod assembly. The fixed hook includes a fixed hook cavity configured to secure a spinal rod. The rod connector also includes a variable hook configured to be rotatably coupled another end of the poly-axial rod. The variable hook includes a variable hook cavity configured to secure another spinal rod. The lateral translation mechanism is configured to change distance between the fixed hook and the variable hook.

18 Claims, 9 Drawing Sheets

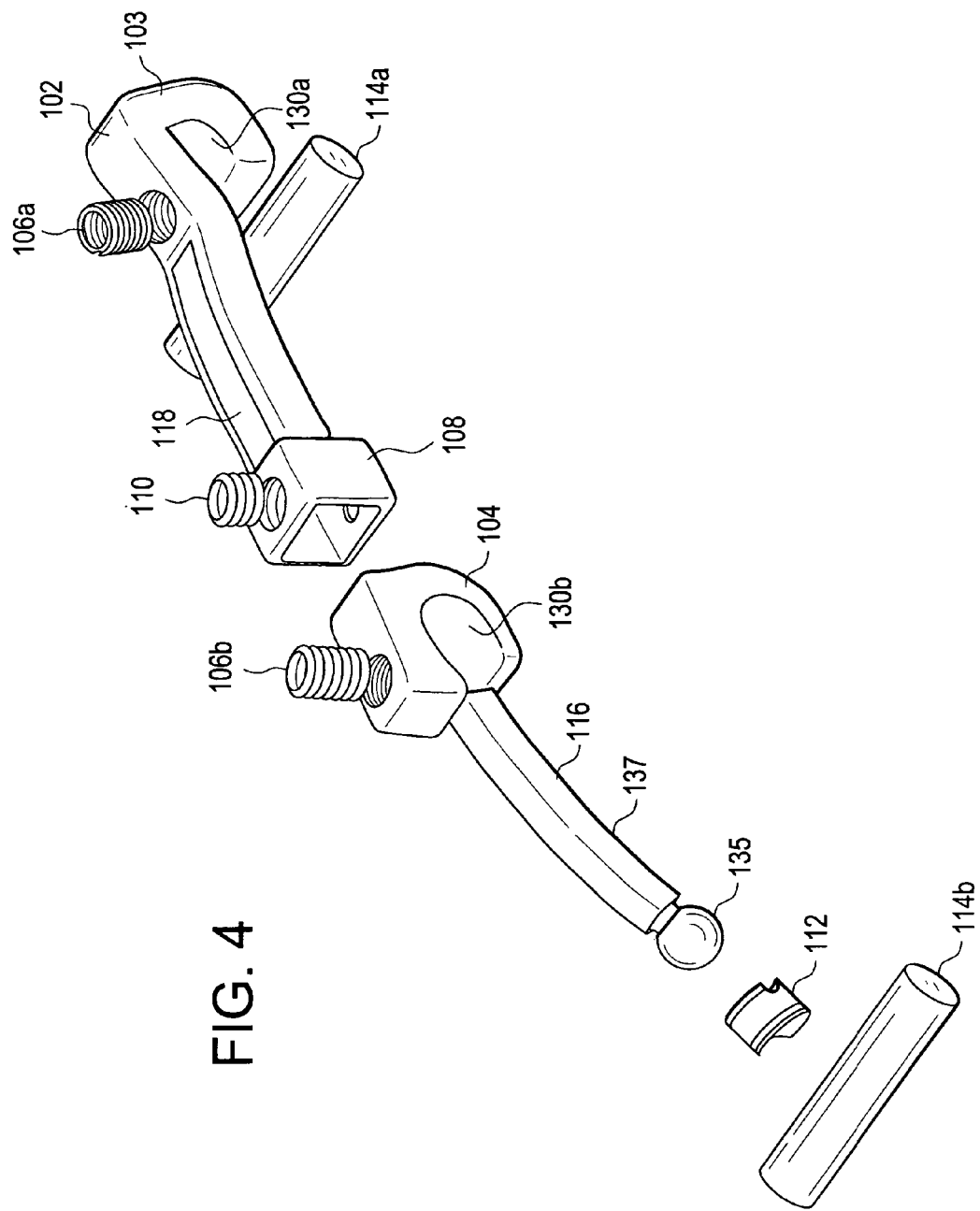

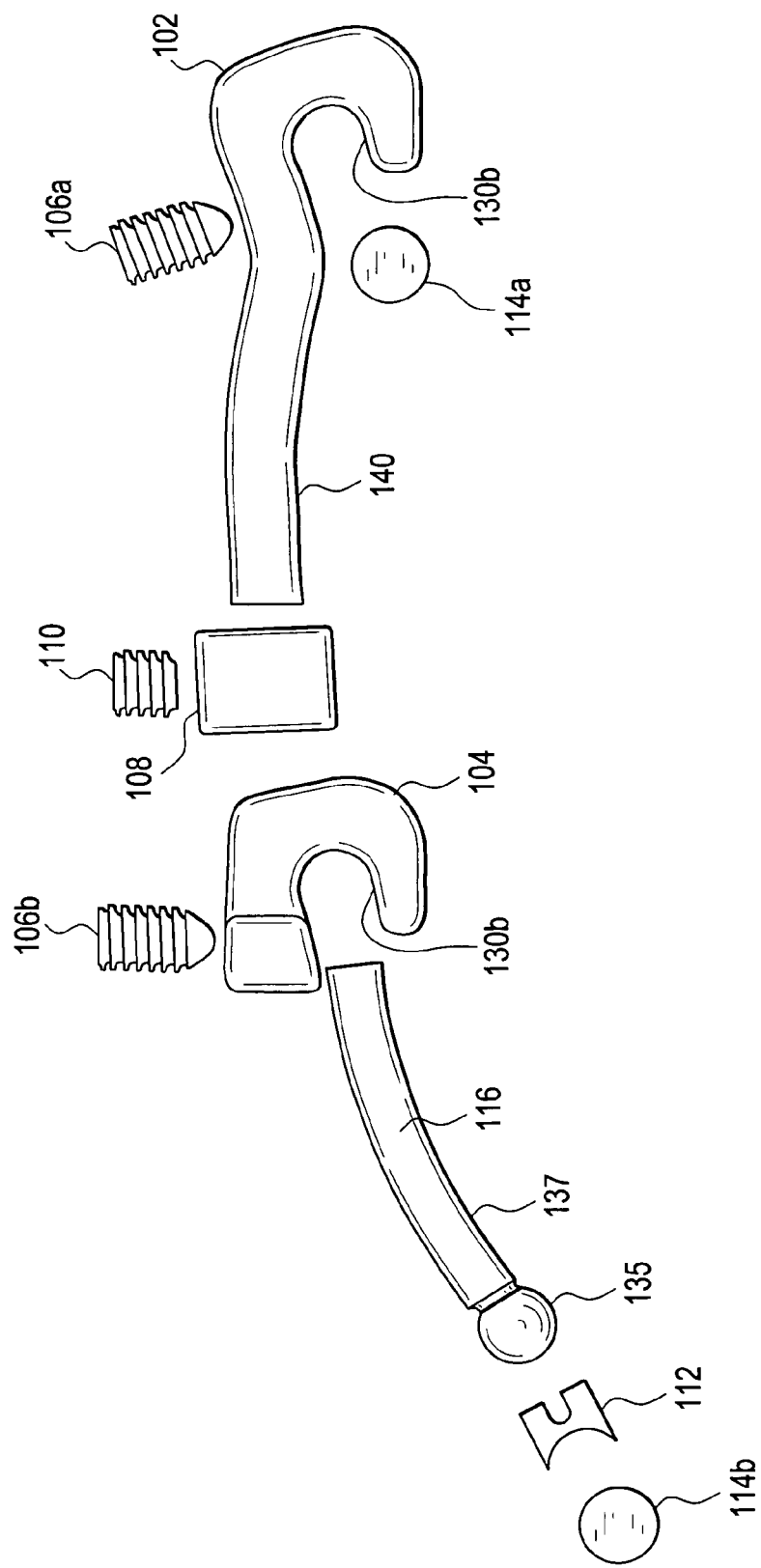

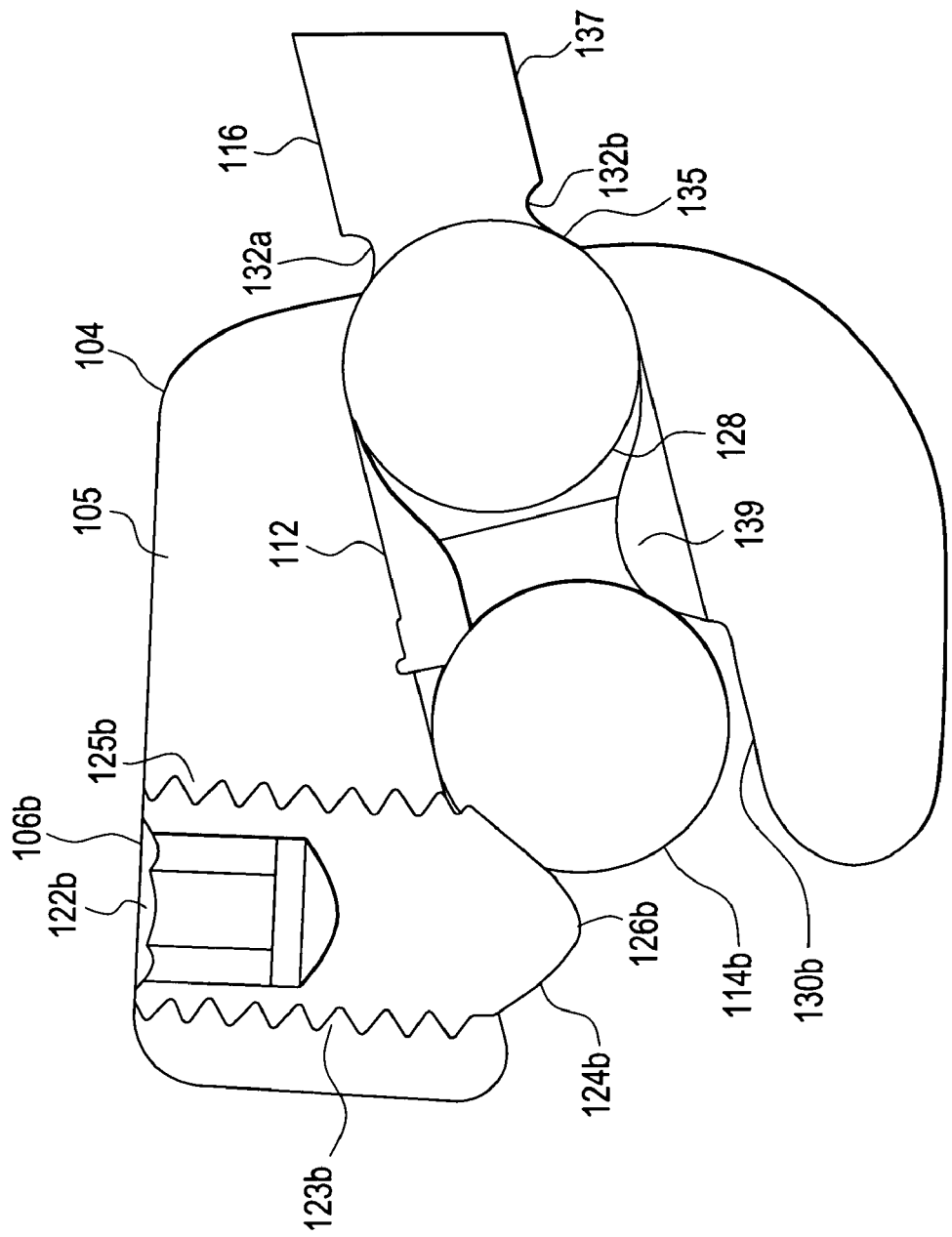

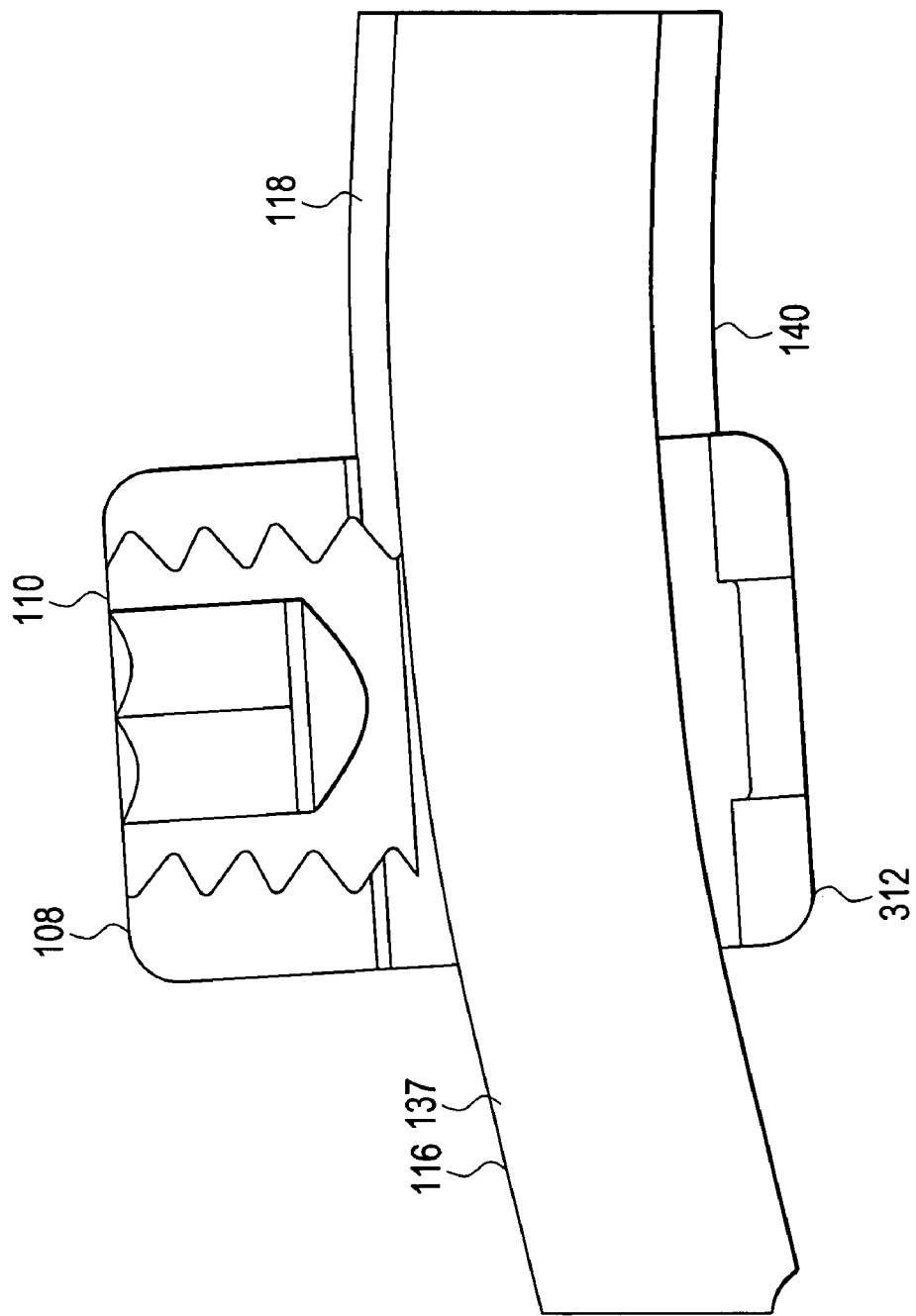

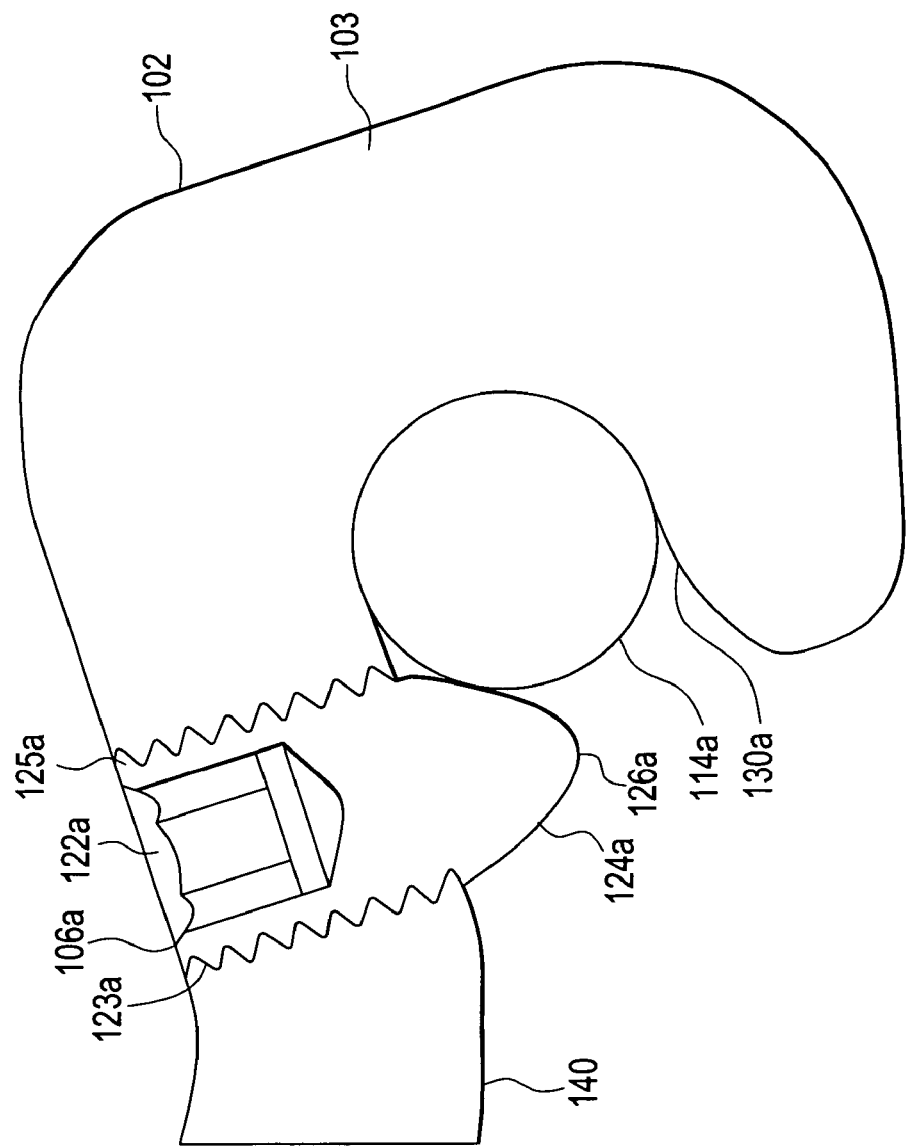

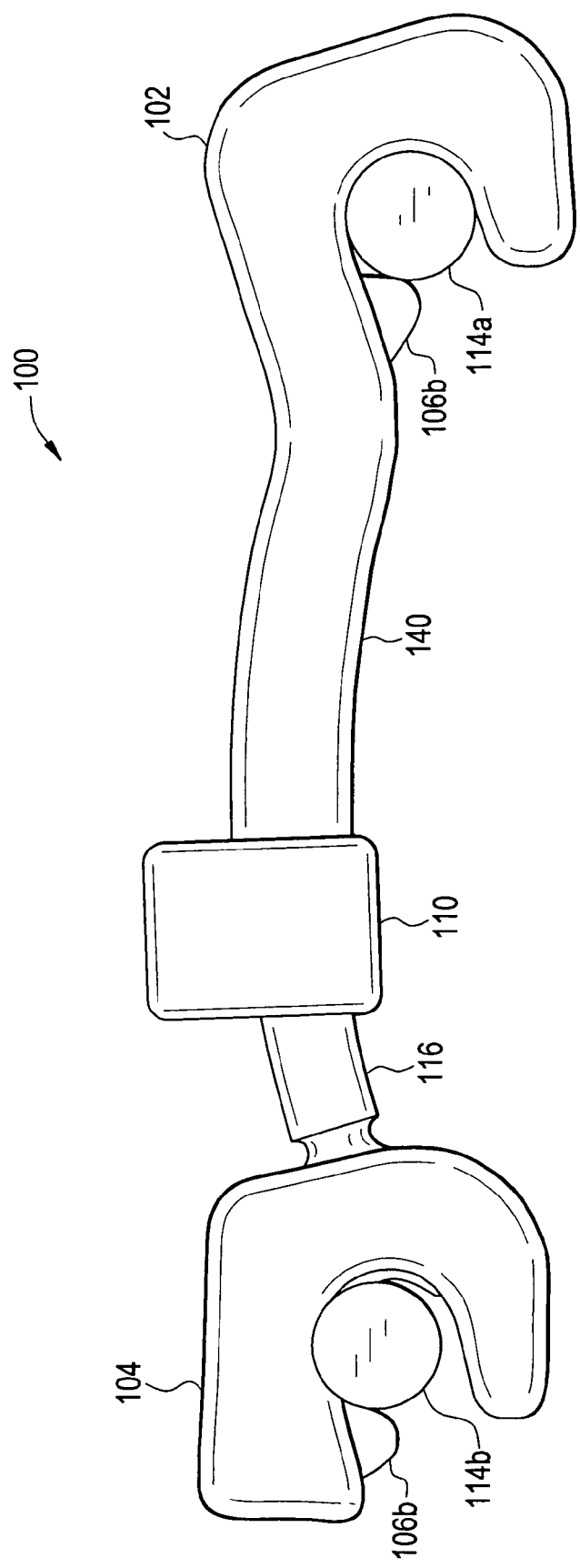

MULTI-AXIAL TRANSVERSE ROD CONNECTOR

CROSS-REFERENCE TO RELATED APPLICATIONS

The present application claims priority to U.S. Provisional Patent Application No. 60/849,871 to Purcell, filed Oct. 6, 2006, entitled "Multiaxial Transverse Rod Connector", and incorporates its disclosure herein by reference in its entirety.

The present application relates to U.S. patent application Ser. No. 11/544,893, to Laurence et al., filed Oct. 6, 2006, entitled "Transverse Rod Connector", which claims priority to U.S. Provisional Application No. 60/725,031, to Laurence et al., filed Oct. 7, 2005, and titled "Transverse Rod Connector", and incorporates entire disclosures of these applications herein by reference.

BACKGROUND OF THE INVENTION

1. Field of the Invention

The present invention relates generally to the field of surgery, and more specifically, to connector devices for connecting and maintaining a spaced apart relationship between bone alignment rods ("transverse rod connectors").

2. Background of the Invention

Spinal fusion is a procedure that promotes fusing or growing together of two or more vertebrae in the spine. Spinal fusion can be performed to:

straighten a spine deformed by scoliosis, neuromuscular disease, cerebral palsy, or other disorder;
prevent further deformation;
support a spine weakened by infection or tumor;
reduce or prevent pain from pinched or injured nerves;
compensate for injured vertebrae or disks.

One of the goals of spinal fusion procedure is to unite two or more vertebrae to prevent them from moving independently of each other. This may be done to improve posture, increase ability to ventilate the lungs, prevent pain, or treat spinal instability and reduce the risk of nerve damage. According to the American Academy of Orthopedic Surgeons, approximately a quarter-million spinal fusions are performed each year, half on the upper and half on the lower spine.

The spine is a series of individual bones called vertebrae, separated by cartilaginous disks. The spine includes seven cervical (neck) vertebrae, 12 thoracic (chest) vertebrae, five lumbar (lower back) vertebrae, and the fused vertebrae in the sacrum and coccyx that help to form the hip region. While the shapes of individual vertebrae differ among these regions, each is essentially a short hollow tube containing the bundle of nerves known as the spinal cord. Individual nerves, such as those carrying messages to the arms or legs, enter and exit the spinal cord through gaps between vertebrae. The spinal disks act as shock absorbers, cushioning the spine, and preventing individual bones from contacting each other. Disks also help to hold the vertebrae together. The weight of the upper body is transferred through the spine to the hips and the legs. The spine is held upright through the work of the back muscles, which are attached to the vertebrae. While the normal spine has no side-to-side curve, it does have a series of front-to-back curves, giving it a gentle "S" shape. The spine curves in at the lumbar region, back out at the thoracic region, and back in at the cervical region.

One of the types of spinal fusion procedures is a posterior spinal fusion surgery. This procedure is performed posteriorly, or from the back of patient, as opposed to anteriorly, or through the abdomen. There are three know posterior fusion techniques (all three are typically performed with pedicle screw fixation). The first is a posterolateral gutter fusion surgery. This type of spinal fusion involves placing bone graft in the posterolateral portion of the spine (a region just outside the back of the spine). The second is a posterior lumbar interbody fusion ("PLIF") surgery. A PLIF involves placing bone graft and/or spinal implant (e.g., cage) directly into the disc space in the front of the spine. The third is a transforaminal lumbar interbody fusion ("TLIF") surgery. A TLIF is essentially like an extended PLIF, as it also involves expanding the disc space by removing one entire facet joint (whereas a PLIF usually involves gaining access to the disc space by removing a portion of the facet joints on each side of the spine).

There have been various approaches and systems for performing posterior spinal surgery. Some conventional systems further include titanium construction that is compatible with current CT and MRI scanning technology, low profile implant systems, top-loading and top-tightening systems, and other parameters. Some systems also include cross-connectors that allow one-piece implant to be applied to a dual-rod construct for a top-loading approach.

The conventional devices and systems have a number of disadvantages. These devices do not provide flexibility when adjusting the devices either prior to, during, or after their placement into the patient. Thus, these devices force a surgeon to utilize a specific configuration, leaving very little room for adjustment in accordance with patient's physiological characteristics and needs. Further, these devices do not allow a surgeon to connect multiple rods by actuating a single setscrew mechanism.

Thus, there is a need for a fixation device that will provide flexibility to a surgeon or other qualified professional when installing and adjusting this fixation device to a particular patient as well as an ability to secure multiple rods of the device.

SUMMARY OF THE INVENTION

Some of the embodiments of the present invention are directed to rod connectors, and more particularly to multi-axial transverse rod connectors configured to secure multiple rods.

Some embodiments of the present invention relate to a device that connects two lateral rods together to increase torsional rigidity of the device. The variability in the device allows it to attach two rods that are not parallel or may/should not be parallel to each other, such as, rods that are diverging or converging.

In some embodiments, multi-axial rod connector can include a variable hook, a fixed hook, at least one rod locking setscrew (two rod locking setscrews), a poly-axial rod, a bushing, a locking connector, and a locking connector setscrew.

Some embodiments of the present invention may include a multi-axial rod connector that is variable and that may include a multi-axial ball and socket joint. Additionally, the device may include a lateral translation mechanism. The multi-axial ball and socket joint may allow unlimited rotational freedom and limited angulation of the device. The lateral translation mechanism may include of a rod, a receiving member, a locking connector, and a locking connector setscrew. The lateral translation mechanism may be used for lateral translation of the components of the multi-axial rod connector. In some embodiments, it may not be possible to rotate components of the multi-axial rod connector using the lateral translation mechanism. Other embodiments may permit rotational movement of certain components.

In some embodiments, the multi-axial ball and socket joint mechanism may be locked to a fixed position by rotating a rod locking setscrew. The rod locking setscrew contacts the rod and forces the bushing to wedge between the spherical portion of the poly-axial rod (i.e., the ball) and the cylindrical portion of the variable hook.

In an another embodiment, the lateral translation mechanism may be locked into a fixed position by rotating the rod locking setscrew. The rod locking setscrew may force the poly-axial rod into the channel of the static link, thereby creating a frictional (or a friction-fit) lock between the two mating surfaces.

The locking capabilities of the device in the present invention provide a number of advantages. The poly-axial locking mechanism may employ a wedging effect along with a cooperation from the bushing structure to lock the device into a static position. The bushing may also act as a compression device that creates friction on the ball portion of the poly-axial rod. This may allow the device to be more stable (rather than free-moving) during insertion of the spinal rods into the multi-axial rod connector.

In yet another embodiment, the lateral translation mechanism can use a separate locking connector to lock the lateral translation of the device. This component may be held in place by mating a "boss" on the bottom of the static link with a "hole" in the bottom of the locking connector. The open channel in the static link allows for manufacturability of the curved channel.

Some embodiments of the present invention relate to a multi-axial rod connector. The connector includes a poly-axial rod assembly configured to include a lateral translation mechanism, a fixed hook configured to be rigidly coupled to one end of the poly-axial rod assembly. The fixed hook includes a fixed hook cavity configured to secure a spinal rod. The device further includes a variable hook configured to be rotatably coupled another end of the poly-axial rod assembly. The variable hook includes a variable hook cavity configured to secure another spinal rod. The lateral translation mechanism is configured to change distance between the fixed hook and the variable hook.

Yet other alternate embodiments of the present invention relate to a method of securing a plurality of spinal rods using a multi-axial rod connector. The multi-axial rod connector includes a poly-axial rod assembly configured to include a lateral translation mechanism, a fixed hook configured to be rigidly coupled to one end of the poly-axial rod assembly. The fixed hook includes a fixed hook cavity configured to secure a spinal rod. The multi-axial rod connector further includes a variable hook configured to be rotatably coupled another end of the poly-axial rod assembly. The variable hook includes a variable hook cavity configured to secure another spinal rod. The lateral translation mechanism is configured to change distance between the fixed hook and the variable hook. The method includes a step of adjusting and fixating the distance between the fixed hook and the variable hook using lateral translation mechanism, inserting the spinal rod into the fixed hook cavity and securing the spinal rod in the fixed hook cavity using a rod locking setscrew, inserting the another spinal rod into the variable hook cavity, rotatably adjusting an orientation of the variable hook, and securing the another spinal rod in the variable hook cavity and fixating the orientation of the variable hook using another rod locking setscrew.

Further features and advantages of the invention, as well as structures and operation of various embodiments of the invention, are further elaborated in detail below with references to the accompanying drawings.

BRIEF DESCRIPTION OF THE DRAWINGS

The present invention is described with reference to the accompanying drawings. In the drawings, like reference numbers indicate identical or functionally similar elements. Additionally, in most circumstances the left-most digit(s) of a reference number identifies the figure number drawing in which the reference number first appears.

FIG. 4 is an exploded perspective view of the exemplary multi-axial rod connector illustrated in FIG. 1.

FIG. 5 is an exploded side view of the exemplary multi-axial rod connector illustrated in FIG. 4.

FIG. 6 is an enlarged side cross-sectional view of a variable hook portion of an exemplary multi-axial rod connector illustrated in FIG. 1.

FIG. 7 is an enlarged side cross-sectional view of a locking connector portion of an exemplary multi-axial rod connector illustrated in FIG. 1.

FIG. 8 is an enlarged side cross-sectional view of a fixed hook portion of an exemplary multi-axial rod connector illustrated in FIG. 1.

FIG. 9 is another side perspective view of the multi-axial rod connector illustrated in FIG. 1

DETAILED DESCRIPTION OF THE INVENTION

Figure 1:
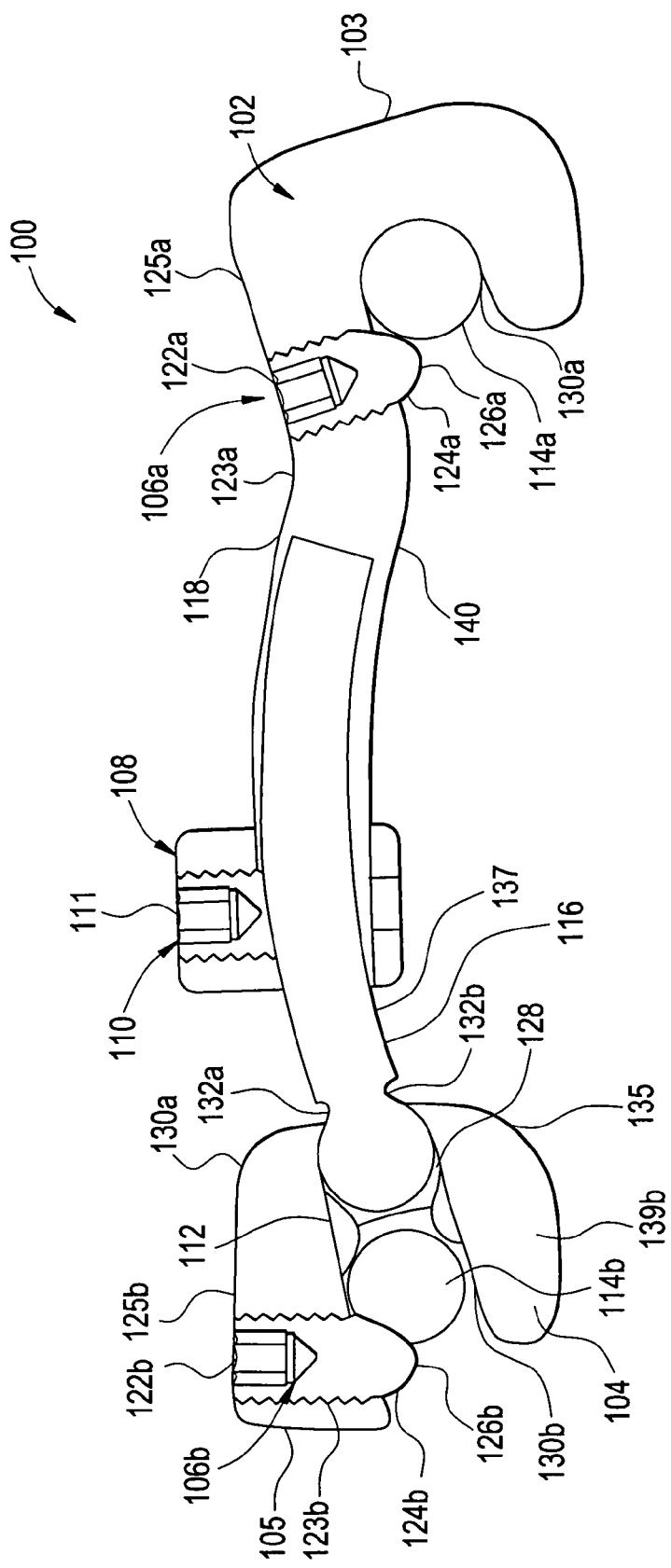
FIG. 1 is a side view of an exemplary multi-axial rod connector, according to some embodiments of the present invention.
Figure 2:
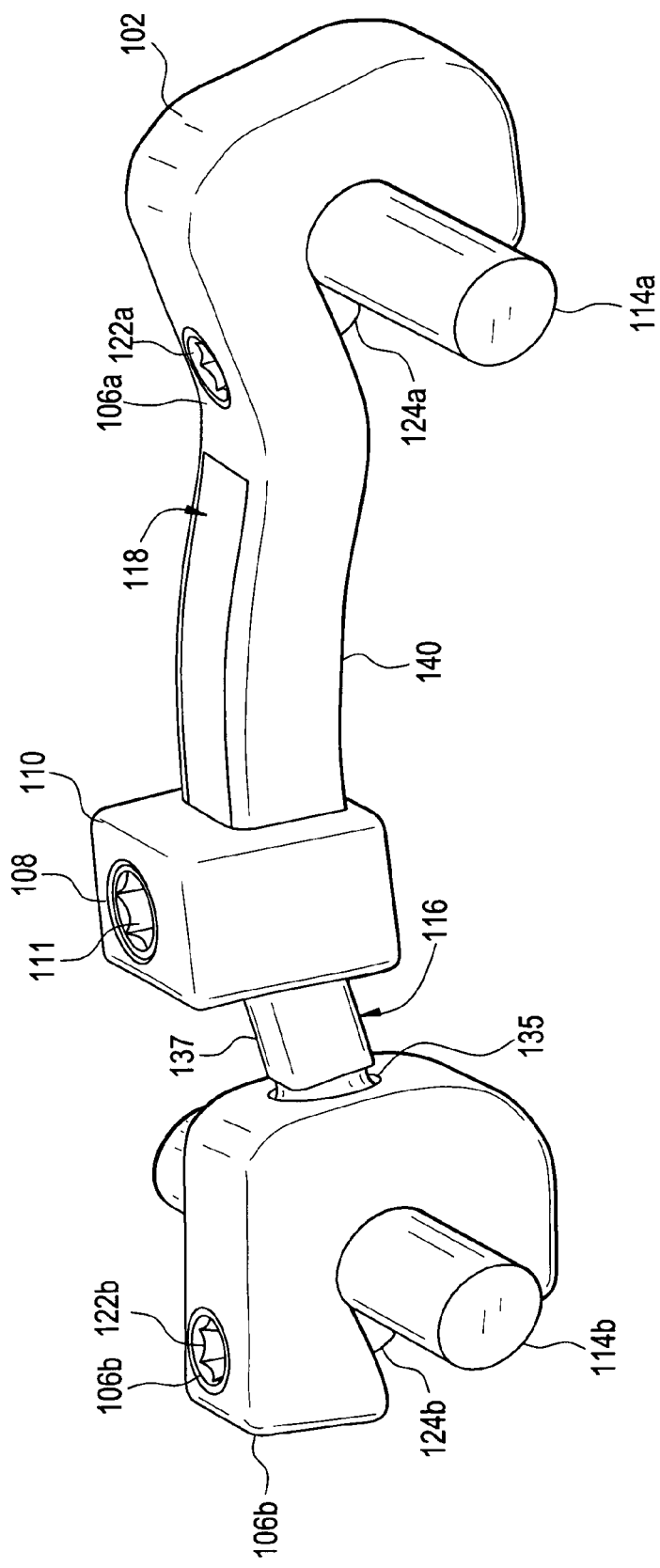
FIG. 2 is a perspective view of an exemplary multi-axial rod connector, according to some embodiments of the present invention.

In some embodiments, the present invention relates to a transverse rod connector that is configured to connect and maintain a spaced-apart relationship between bone alignment rods.

FIGS. 1-9 illustrate an exemplary multi-axial transverse rod connector 100, according to some embodiments of the present invention. The connector 100 includes a fixed hook 102, a variable hook 104, rod locking setscrews 106 (*a, b*), a multi-axial or poly-axial connector rod 116, and a locking connector 108 having a locking connector setscrew 110. The hooks 104 and 102 are configured to accommodate placement and securing of connector rods 114*a* and 114*b*. Connector rods 114 can be spinal connector rods or any other rods used in surgical procedures. The rods 114 can be secured at any angles and/or axial planes with regard to each other (e.g., rods can be converging, diverging, parallel, perpendicular to each other, etc.).

The fixed hook 104 further includes a housing 103 having a poly-axial rod assembly or an extended portion 140, as shown in FIGS. 1 and 8. The extended portion 140 includes a channel 118 that is configured to accommodate expansion rod 116. The rod 116 is configured to translate inside the channel 118 for expansion of the rod connector 100, as shown in FIG. 1. As shown in FIGS. 4 and 5, the rod 116 has a square shape that matches the square shape of the channel 140. In some embodiments, the rod 116 has a substantially shape that matches the round shape of channel 118 and can be configured to rotate inside the channel 118. By translating the rod 116 inside the channel 118, a medical professional (e.g., surgeon) can adjust the distance between the fixed hook 104 and the variable hook 102.

The fixed hook housing 103 is configured to include a cavity 130a. The variable hook housing 105 is configured to include a cavity 130b. The cavity 130a is configured to accommodate placement of the spinal rod 114a. The cavity 130b is configured to accommodate placement of the spinal rod 114b. As illustrated in FIG. 1, the cavities 130 are configured to have round shape so that they can accommodate placement of round rods 114, as shown in FIGS. 6 and 8. As can be understood by one skilled in the art, the shapes of the cavities 130 (as well as rods 114) can be different in order to accommodate variable shape spinal rods 114.

The spinal rods 114 are secured within the cavities 130 by way of rod locking setscrews 106(a, b). The rod locking setscrews 106(a, b) are configured to be inserted into openings 125(a, b) of housings 103 and 105, respectively. The openings 125 are configured to include threading that interacts with threading 123(a, b) of the setscrews 106. The rod locking setscrews 106 are further configured to include housings 124(a, b), respectively. The housings 124 further include tips 126(a, b) that interact with rods 114 and allow securing of the rods 114 within cavities 130 of the hooks 102 and 104. The housings 124 of the setscrews 106 also include cavities 122(a, b), respectively, in their top portions. The cavities 122 are configured to accommodate insertion of a tool (not shown in FIG. 1) that can be used by a surgeon or any other medical professional (or any other user) to "screw-in" rod locking setscrews 106 into the openings 125, respectively. Once the rod 114 is placed inside the cavity 130, the user can insert the tool (not shown) into the cavity 122 of the setscrew 106 and rotate/twist the tool, and thereby the setscrew 106, to rotate the setscrew 106 in a downward direction until the tip 126 begins to interact with the rod 114. By rotating the setscrew 106 in the downward direction, the setscrew 106 pushes the rod 114 into the cavity 130 and further secures the rod 114 inside the cavity 130. As illustrated in FIG. 1, the tip 126 of the rod's housing 124 is configured to interact with the rod 114 and prevent rod 114 from falling out of the cavity 130. As can be understood by one skilled in the art, the rotation of the setscrew 106 can be in a clockwise or counterclockwise direction. Further, the cavity 130 and the setscrew 106 can be configured to accommodate any size spinal rod 114. To accommodate a smaller diameter spinal rod 114, the setscrew 106 can be further rotated until the tip 126 interacts with the rod 114 and secures the rod inside the cavity 130. Further, the cavity 122 inside the setscrew 106 is configured to include a plurality of sides that can be configured to accommodate placement of a polygon-shaped tool. As can be understood by one skilled in the art, the cavity 122 can be configured to accommodate any tool. Further, the rod locking setscrew 106 can be configured to screw-in, snap-in, lock-in, or be otherwise secured inside the openings 125 in any way as to prevent escape of the spinal rod 114 from the cavity 130. Further, setscrews 106 can be any locking mechanisms that are configured to create compression on the rods 114.

Figure 3:
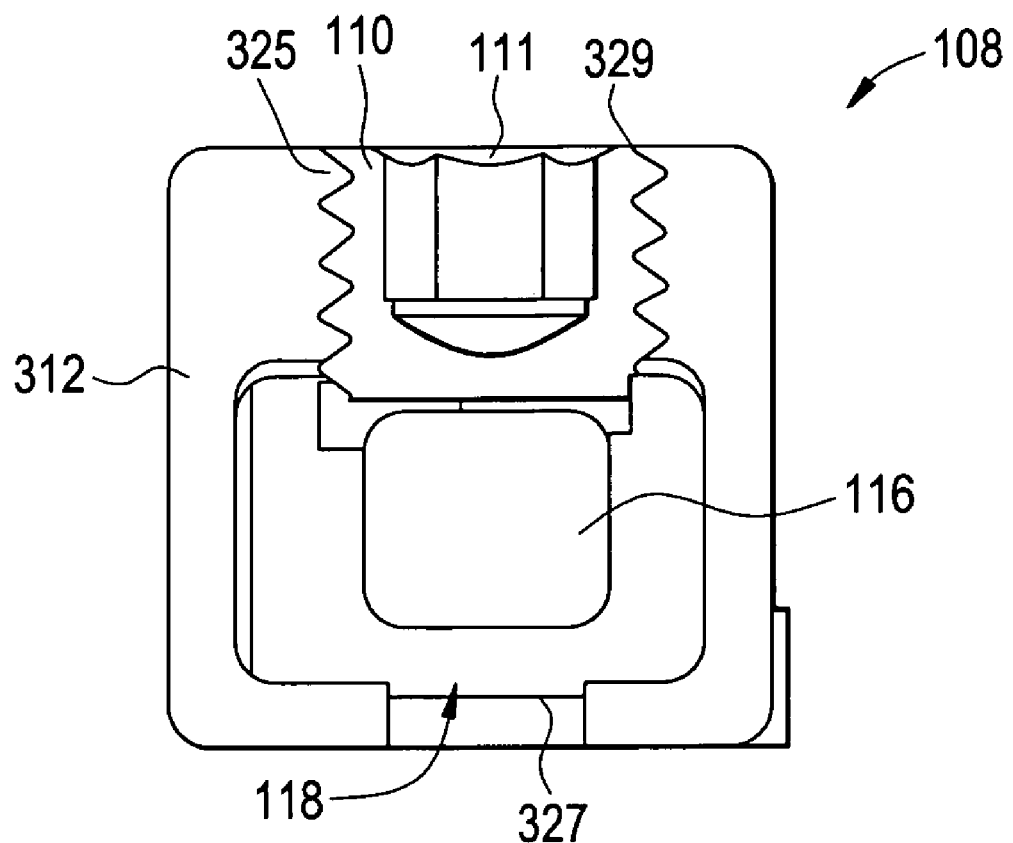
FIG. 3 is a side view of a locking connector of the exemplary multi-axial rod connector illustrated in FIG. 2.

The housing 103 of the fixed hook 102 further includes a locking connector 108 having a locking connector setscrew 110. In some embodiments, the combination of the channel 118 and the locking connector can be referred to as a translation mechanism of the rod connector 100. The locking connector 108 is configured to secure the poly-axial rod 116 at a particular location in the channel 118. The locking connector 108 can be configured to be disposed anywhere along the extended portion 140 of the housing 103. As illustrated in FIG. 1, the locking connector 108 is configured to be disposed at the end of the extended portion 140 so that the cavity 130a and the locking connector 108 are configured to be disposed on the opposite ends of the housing 103. The locking connector 108 is configured to secure the rod 116 in a similar fashion as the setscrews 106 secure the spinal rods 114 inside cavities 130. Referring to FIG. 3, the connector 108 includes a housing 312 configured to accommodate placement of the setscrew 110. The housing 312 that includes an opening 329 at its top having a threading 325 disposed along the sides of the opening 329, as illustrated in FIG. 3. The housing 312 further includes an opening 327 that is configured to allow placement of the extended portion 140 of the housing 103 along with the channel 118 containing rod 116. As can be understood by one skilled in the art, the opening 327 is configured to allow friction-fit, loose-fit, or any other placement of the extended portion 140.

The opening 329 is configured to connect the outside of the housing 312 with the opening 327. Further, the opening 329 can have a size that substantially equal to the open channel 118. As can be understood by one skilled in the art, the opening 329 can have any size. The setscrew 110 is configured to include threading that interacts with the threading 325 of the housing 312. The setscrew 110 is further configured to include an opening 111 that is similar to openings 122 of the setscrews 106. The opening 111 accommodates a tool (not shown) is configured to rotate the setscrew 110 inside the opening 329. As the setscrew 110 rotates in a downward direction, it pushes the rod 116 in a downward direction towards sides of the open channel 118. By pushing the rod 116, the setscrew 110 is configured to secure the rod 116 inside the channel 118. Such arrangement can be referred to as a "boss and hole" arrangement.

The rod 116 includes a multi-axial ball or a rounded portion 135 and an elongated portion 137. The elongated portion 137 is configured to be contained within channel 118. The rounded portion 135 is configured to be rotatably secured within the housing 105 of the variable hook 104, as shown in FIGS. 1 and 6. The housing 105 is configured to include a socket joint or a cavity 128 that is configured to accommodate placement of the rounded portion 135. Indentations 132 (a, b) are placed between the elongated portion 137 and the rounded portion 135. The indentations 132 are configured to allow rotation of the rounded portion 135 within the cavity 128 (or alternatively, allow rotational motions of the variable hook 104 about the rounded portion 135) and further configured to prevent sliding of the rounded portion 135 from the cavity 128. The rotational motions can be performed in any direction. The indentations 132 are also configured to prevent sliding of the elongated portion 137 into the cavity 128. In some embodiments, the rounded portion 135 of the rod 116 and the cavity 128 can be configured as a "ball-and-socket" type arrangement. The cavity 128 and the rounded portion 135 are configured to permit angulation of the variable hook 104 with regard to the fixed hook 102. In some embodiments, the angulation can be limited.

The cavity 128 and the cavity 130b can be configured as a unitary opening created in the housing 105 of the hook 104. This unitary opening is further configured to accommodate placement of a bushing 112 along with rounded portion 135 and the spinal rod 114b, as illustrated in FIGS. 1, 4, and 5. The bushing 112 separates the rounded portion 135 of the rod 116 and the spinal rod 114b and, thus, prevents encroachment of the rounded portion 135 onto the spinal rod 114b and vice versa. The bushing 112 further includes convex portions 139a and 139b configured to protrude towards each other inside the bushing 112. The convex portions 139 interact with the rounded portion 135 of the rod 116 and the rod 114b. As illustrated in the FIG. 1's cross-sectional view of rod connector 100, the convex portion 139a is located at the top of the bushing 112 and the convex portion 139b is located at the bottom of the bushing 112. As can be understood by one skilled in the art, there can be more than one convex portion 139 located inside the bushing 112. Alternatively, a single protrusion 139 can be disposed in a circular fashion along the inner circumference of the bushing 112. FIGS. 4 and 5 illustrate a substantially circular bushing 112 that is configured to fit inside the unitary opening created by cavities 130b and 128. As can be understood by one skilled in the art, other shapes and sizes of the bushing 112 are possible.

FIGS. 4 and 5 are perspective and side exploded views of the rod connector 100 illustrated in FIG. 1, respectively. In order to assemble rod connector 100, the following steps may be performed. As can be understood by one skilled in the art, the present invention is not limited to the order of steps discussed below.

The rod 116 is inserted through the cavity 130b and cavity 128 of the variable hook 104 until elongated portion 137 of the rod 116 extends away from the housing 105 of the hook 104 and the rounded portion 135 of the rod 116 is disposed inside the cavity 128 having indented portions 132 protrude away from the housing 105 as well.

The extended portion 140 of the housing 103 of the fixed hook 102 is inserted into the opening 327 of the locking connector 108. The insertion is made so that the locking connector setscrew 110 (which is inserted into the opening 329, as shown in FIG. 3) is located on top of the channel 118 of the extended portion 140, as illustrated in FIG. 3. The setscrew 110 is then rotated in a downward direction to secure the rod 116 inside the channel 116. As can be understood by one skilled in the art, the setscrew 110 can be secured at any location on the extended portion 140 as well as can secure the rod 116 at any distance away from the extended portion 140. Further, the position of the setscrew 110 and the rod 116 can be adjusted as desired.

The spinal rod 114a is secured inside the cavity 130a of the fixed hook 102 using setscrew 106a that is rotated in a downward direction to push the rod 114a towards the walls of the cavity 130a.

The bushing 112 is then partially inserted into the cavity 130b and cavity 128 until its convex portions 139 are substantially adjacent and/or begin to interact with the rounded portion 135 of the rod 116. Because the portion 135 is substantially round, the variable hook 104 can be configured to rotate around the portion 135 and secure rods 114 at any angle with regard to each other (including parallel, perpendicular, or any other angle orientation).

The rod 114b is inserted into the cavity 130b until it is substantially adjacent and/or begins to interact with the convex portions 139 of the bushing 112. Then, to secure the rod 114b, the setscrew 106b is inserted into the opening 123b in the housing 105 of the variable hook 104 and rotated in a downward direction to push the rod 114b against the convex portions 139 of the bushing 112.

In some embodiments, to prevent bushing 112 from sliding between cavities 128 and 130b and allow fixed engagement of the rod 114b and rotatable engagement of the rod 116 inside appropriate cavities, the unitary opening created by cavities 130b and 128 can be configured to have a smaller radius at the cavity 128 than at the cavity 130b. The radius can be configured to gradually decrease from cavity 130b to cavity 128. In some embodiments, in order to prevent the busing 112 from sliding in and out of the cavities 128 and 130b, a stopper device (not shown) can be included, thereby preventing bushing 112 from sliding further into the cavity 128. This allows free rotational movement of the rounded portion 135 inside the cavity 128. Such rotational movement of the rounded portion 135 allows adjustable securing of spinal rods 114 as compared to the fixed securing. As can be understood by one skilled in the art, the rods can be fixedly secured as well.

In some embodiments, the present invention relates to a method of securing a plurality of spinal rods using the multi-axial rod connector 100 discussed above with regard to FIGS. 1-9. The method includes steps of adjusting and fixating the distance between the fixed hook 102 and the variable hook 104 using the lateral translation mechanism 140. Then, the spinal rod 114a is inserted into the fixed hook cavity 130a and the spinal rod 114b is secured in the fixed hook cavity 130a using the rod locking setscrew 106a. The spinal rod 114a is then inserted into the variable hook cavity 130b and orientation of the variable hook 104 is rotatably adjusted. The spinal rod 114b is secured in the variable hook cavity 130b and orientation of the variable hook 104 is fixated using rod locking setscrew 106b.

The rod connector 100 including its various parts and/or portions can be manufactured from any biocompatible material such as titanium, stainless steel, polyetheretherketone ("PEEK"), or any other material. In some embodiments, the rod connector 100 can provide spacing of 25 millimeters ("mm") to 95 mm between spinal rods 114. In other embodiments, the rod connector 100 can provide spacing of 35 mm to 85 mm between rods 114. In yet other embodiments, the spacing can be 45 mm to 75 mm. In yet other embodiments, the spacing can be 55 mm to 65 mm.

The rod connector 100 can secure spinal rods 114 having diameters between 3.0 mm to 6.5 mm. In some embodiments, the rod diameters can be 3.0 mm. Alternatively, the rod diameters can be 3.5 mm, 5.5 mm, 6.35 mm, etc. The rod 100 can secure spinal rods 114 that have different diameters from one another.

Example embodiments of the methods and components of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments, but should be defined only in accordance with the following claims and their equivalents.

What is claimed:

1. A multi-axial rod connector, comprising:
a poly-axial rod assembly configured to include a lateral translation mechanism;
a fixed hook configured to be rigidly coupled to a first end of said poly-axial rod assembly, wherein said fixed hook includes a fixed hook cavity configured to secure a first spinal rod;
a variable hook configured to be rotatably coupled to a second end of said poly-axial rod assembly, wherein said variable hook includes a variable hook cavity configured to secure a second spinal rod;
a bushing disposed between said second end of said poly-axial rod assembly and said second spinal rod; and
a second rod locking setscrew disposed within said variable hook on an opposite side of said second spinal rod as said poly-axial rod assembly and configured to contact said second spinal rod to force said second spinal rod against said bushing and towards said second end of said poly-axial rod assembly,
wherein said lateral translation mechanism is configured to change distance between said fixed hook and said variable hook.

2. The multi-axial rod connector according to claim 1, wherein said fixed hook comprises a first rod locking setscrew configured to secure said first spinal rod in said fixed hook cavity.

3. The multi-axial rod connector according to claim 1, wherein said lateral translation mechanism comprises
- an open channel configured to be disposed in said poly-axial rod assembly;
- a poly-axial rod configured to be disposed in said open channel and further configured to laterally translate within said open channel;
- a locking connector configured to be coupled to said poly-axial rod; and
- a locking connector setscrew configured to be disposed in said locking connector and further configured to lock said poly-axial rod in said open channel.

4. The multi-axial rod connector according to claim 3, further comprising a multi-axial ball configured to be coupled to said poly-axial rod and a socket joint configured to receive said multi-axial ball wherein said socket joint is configured to permit rotational movement of said multi-axial ball within said socket joint.

5. The multi-axial rod connector according to claim 4, wherein said multi-axial ball and said socket joint are configured to permit limited angulation of said variable hook with respect to said fixed hook.

6. The multi-axial rod connector according to claim 4, wherein said bushing is configured to rigidly secure said multi-axial ball to said socket joint.

7. The multi-axial rod connector according to claim 6, wherein said multi-axial ball is rigidly secured to said socket joint when said second spinal rod is placed into said variable hook cavity and said second rod locking setscrew is applied to secure said second spinal rod in said variable hook cavity.

8. The multi-axial rod connector according to claim 7, wherein, when applied, said second rod locking setscrew is configured to laterally move said second spinal rod toward said bushing and cause said second spinal rod to contact said bushing;
- wherein said contact of said second spinal rod and said bushing is configured to cause said bushing to contact said multi-axial ball and secure said multi-axial ball in said socket joint.

9. The multi-axial rod connector according to claim 1, wherein said distance between said fixed hook and said variable hook is in the range between 25 mm and 95 mm.

10. The multi-axial rod connector according to claim 1, wherein at least a portion of the multi-axial rod connector is manufactured from a biocompatible material.

11. A method of securing a plurality of spinal rods using a multi-axial rod connector,
wherein the multi-axial rod connector includes
- a poly-axial rod assembly configured to include a lateral translation mechanism,
- a fixed hook configured to be rigidly coupled to a first end of the poly-axial rod assembly, wherein the fixed hook includes a fixed hook cavity configured to secure a first spinal rod,
- a variable hook configured to be rotatably coupled to a second end of the poly-axial rod assembly, wherein the variable hook includes a variable hook cavity configured to secure a second spinal rod;
- a bushing disposed between said second end of said poly-axial rod assembly and said second spinal rod; and
- a second rod locking setscrew disposed within said variable hook on an opposite side of said second spinal rod as said poly-axial rod assembly and configured to contact said second spinal rod to force second spinal rod against said bushing and towards said second end of said poly-axial rod assembly,
and wherein the lateral translation mechanism is configured to change distance between the fixed hook and the variable hook,
comprising the steps of
- adjusting and fixating the distance between the fixed hook and the variable hook using the lateral translation mechanism;
- inserting the first spinal rod into the fixed hook cavity and securing the first spinal rod in the fixed hook cavity using a first rod locking setscrew;
- inserting the second spinal rod into the variable hook cavity;
- rotatably adjusting an orientation of the variable hook;
- securing the second spinal rod in the variable hook cavity; and
- adjusting said second rod locking setscrew to force said second spinal rod and said bushing towards said second end of said poly-axial rod assembly.

12. The method according to claim 11, wherein the lateral translation mechanism comprises
- an open channel configured to be disposed in the poly-axial rod assembly;
- a poly-axial rod configured to be disposed in the open channel and further configured to laterally translate within the open channel;
- a locking connector configured to be coupled to the poly-axial rod; and
- a locking connector setscrew configured to be disposed in the locking connector and further configured to lock the poly-axial rod in the open channel.

13. The method according to claim 12, wherein said adjusting and fixating step further comprises
- adjusting position of the poly-axial rod in the open channel; and
- fixating the position of the poly-axial rod in the open channel using a locking connector and a locking connector setscrew.

14. The method according to claim 12, wherein the multi-axial rod further includes a multi-axial ball configured to be coupled to the poly-axial rod and a socket joint configured to receive the multi-axial ball;
wherein said rotatably adjusting step further comprises rotatably moving the multi-axial ball within the socket joint.

15. The method according to claim 14, said rotatably adjusting step further comprises limiting angulation of the variable hook with respect to the fixed hook.

16. The method according to claim 14, wherein said securing and fixating steps further comprise;
- rigidly securing the multi-axial ball to the socket joint.

17. The method according to claim 16, wherein said rigidly securing step further comprises;
- applying force to said second locking setscrew to secure the second spinal rod in the variable hook cavity.

18. The method according to claim 17, wherein said applying step further comprises
- laterally moving the second spinal rod toward the multi-axial ball;
- and fixating the multi-axial ball in the socket joint.

* * * * *